(12) United States Patent
Fukuoka

(10) Patent No.: US 8,551,922 B1
(45) Date of Patent: Oct. 8, 2013

(54) PROCESS OF FABRICATING TISSUE ARRAY

(71) Applicant: Junya Fukuoka, Toyama (JP)

(72) Inventor: Junya Fukuoka, Toyama (JP)

(73) Assignee: National University Corporation University of Toyama, Toyama-Shi (JP)

( * ) Notice: Subject to any disclaimer, the term of this patent is extended or adjusted under 35 U.S.C. 154(b) by 0 days.

(21) Appl. No.: 13/845,195

(22) Filed: Mar. 18, 2013

Related U.S. Application Data

(62) Division of application No. 12/449,865, filed as application No. PCT/JP2008/053965 on Mar. 5, 2008, now abandoned.

(30) Foreign Application Priority Data

Mar. 7, 2007 (JP) ................. 2007-056884

(51) Int. Cl.
*C40B 50/00* (2006.01)
*C40B 60/10* (2006.01)
*A01N 1/02* (2006.01)

(52) U.S. Cl.
USPC ............... 506/23; 506/39; 435/1.1; 435/40.5; 435/40.52

(58) Field of Classification Search
USPC ................... 435/1.1, 40.5, 40.52; 506/23, 39
See application file for complete search history.

*Primary Examiner* — Christopher M Babic
*Assistant Examiner* — Jeremy C Flinders
(74) *Attorney, Agent, or Firm* — Manabu Kanesaka

(57) ABSTRACT

In a process of fabricating a tissue array, a tissue block is sliced to obtain sheet-form pieces of tissue, and each of the sheet-form pieces is closely rolled around a guide member to form a spiral shape tissue around the guide member. Then, the spiral shape tissues are inserted in an axial direction into holes arrayed in a base block.

4 Claims, 13 Drawing Sheets

(a)

(b)

(c)

(a)

(b)

(c)

(d)

(e)

(a)

(b)

(c)

(d)

PROCESS OF FABRICATING TISSUE ARRAY

CROSS-REFERENCE TO RELATED APPLICATION

This is a divisional application of Ser. No. 12/449,865 filed on Oct. 20, 2009, which is based on PCT/JP2008/053965 filed on Mar. 5, 2008 claiming a priority of Japanese Patent Application No. 2007-056884 filed on Mar. 7, 2007.

TECHNICAL FIELD

The present invention relates to a process of fabricating a tissue array.

BACKGROUND ART

A tissue array chip having pieces of tissue disposed on a substrate has heretofore been used for the examination or analysis of body tissue. The tissue array chip is used for the examination of presence or absence of diseased tissue, the analysis of a gene or protein, screening, etc. through application of a stain solution for specifically staining a test substance to the test substance.

The tissue array chip is fabricated in the following manner. FIG. 11 is an explanatory view illustrating a conventional process of fabricating a tissue array chip. In step (a), body tissue is formed into a tissue block that is then punched to collect cores. In step (b), the collected cores are inserted into holes arrayed on and formed in a base block. In step (c), the surface of the base block having the cores inserted into the holes is sliced on the order of several μm to fabricate tissue array sheets each having pieces of tissue disposed thereon. In step (d), a tissue array sheet is mounted on a substrate to fabricate a tissue array chip. Steps (c) and (d) are taken repeatedly to fabricate plural tissue array chips.

A tissue array block used for the fabrication of the tissue array chip is fabricated using a device equipped with a punching system. Patent Document 1 discloses a device equipped with a punch for a base block and a punch for a tissue block. The device uses the punch for the base block to form holes in the base block, punches the tissue block using the punch for the tissue block to collect cores and inserts the collected cores into the holes in the base block, thereby fabricating a tissue array block.

Patent Document 1: JP-A 2004-215667

DISCLOSURE OF THE INVENTION

Problems the Invention Intends to Solve

However, the conventional technique entails the following problems (1) to (7). As problem (1), tissue blocks have a variety of sizes and possibly have a small thickness from the beginning of collection. Furthermore, since the tissue blocks are used while being chipped off a number of times during the course of the examination or analysis thereof, they are gradually reduced in thickness. For these reasons, in fabricating a tissue array chip, there is a case where cores having a sufficient length cannot be obtained, resulting in extreme reduction in number of tissue array chips capable of being fabricated or failure to fabricate a tissue array chip.

As problem (2), the tissue blocks have different degrees of hardness depending on the kind of tissue. For this reason, situations have arisen, in which the insertion of a punch fails to core the tissue blocks and in which the punch is damaged. A technique of stably collecting cores from the tissue blocks with the punch requires a lot of skill.

Problem (3) is shown in FIG. 12, in which (a) is a schematic cross section of a tissue block illustrating cores collected when exemplifying a paraffin-embedded tissue block, (b) is a schematic cross section of a tissue array block having the cores embedded therein, and (c) includes schematic plan views of tissue array chips fabricated from the tissue array block. As shown in (a), since the tissue block is amorphous, cores collected from plural tissue blocks or from different places of a single tissue block have portions of tissue t irregular in length. For this reason, when slicing the tissue array block to fabricate tissue array chips, as shown in (b) and (c), for example, pieces of tissue t emerge in all the cores when the slicing position is at the neighborhood L1 of the surface layer of the tissue array block, whereas at a deep position as shown by L2 there are cores in which pieces of tissue t fail to emerge. Thus, there is a case where the pieces of tissue have a defect depending on the slicing position.

Though a site of interests a of diseased tissue in a tissue block is specified to selectively collect cores when including the site of interests a in a tissue array chip as a target, problem (4) is posed in FIG. 13, in which (a) is a schematic cross section of the tissue block illustrating cores collected when using the site of interests a as the target, (b) is a schematic cross section of a tissue array block having the cores embedded therein, and (c) includes schematic plan views of tissue array chips fabricated from the tissue array block. As shown in (a), the site of interests a contained in the tissue block is amorphous and, even when it is included in the surface layers of the cores, there is a case where it is not included in the lower layers of the cores. For this reason, when slicing the tissue array block to fabricate tissue array chips, as shown in (b) and (c), for example, all the cores contain sites of interests a when the slicing position is in the neighborhood L1 of the surface layer, whereas when the slicing position is in the neighborhood of the lower layer as shown by L2, there is a case where the sites of interests a are not contained in the cores. Thus, the sites of interests a have a defect depending on the slicing position.

Problem (5) is imposed on examination of the presence or absence of a site of interests of diseased tissue. To be specific, though it is preferred from the standpoints of reliability and precision of analysis that cores are collected from regions more dispersed, since the cores to be collected are limited to local portions of a tissue block in a process by punching, the reliability of examination and the precision of analysis have their own limits.

Problem (6) is raised in that when one of the tissue block and the core on the tissue array chip contains a site of interests a, it is desired to specify a place of the other corresponding to the site of interests. FIG. 14 is an explanatory view illustrating the positional relationship between a site of interests a contained in the core on the tissue array chip and a site of interests a on the surface of the tissue block. When cores have been collected from the tissue block, the relationship between the position within the core (the site of interests a in FIG. 14) and the position within the tissue block (position indicated by arrow e in FIG. 14) is difficult to establish and, therefore, it is very difficult to specify a place corresponding to the site of interests a.

Problem (7) is entailed in that when cores have been collected from the tissue block by punching, tissue of the place of the tissue block from which the cores are collected suffers a defect. On the other hand, the tissue block is used for various examinations and analyses after collecting the cores. For this reason, when using the tissue block for the examination or analysis after collecting the cores, the tissue of the place of collection cannot be used anymore and, particularly when the place of collection contains an important site, the influence of the non-reusability becomes large.

The present invention has been proposed in view of the aforementioned state of affairs and the object thereof is to provide a process of fabricating a tissue array block; a process of fabricating a tissue array sheet; a tissue array block and a tissue array chip; and a system of fabricating a tissue array block and a system of fabricating a tissue array sheet used for these, in which the tissue array block can be fabricated even in the case of that having a small thickness, is little affected by tissue hardness and, when having been processed into a tissue array chip, does not suffer any defect in a piece of tissue or at a site of interests, enables the collection of pieces of tissue from an area dispersed more than conventionally, also enables the establishment of positional relationship between the inside of a tissue piece and the inside of a tissue block, and scarcely affects the utilization of the tissue block remaining after collecting the pieces of tissue.

Means for solving the Problems

A process of fabricating a tissue array block according to the present invention comprises the steps of slicing a tissue block to obtain roll-shaped pieces of tissue and inserting the roll-shaped pieces of tissue in an axial direction into holes arrayed in a base block. In addition, a process of fabricating a tissue array block according to the present invention comprises the steps of slicing a tissue block to obtain sheet-like pieces of tissue, coiling and rolling the sheet-like pieces of tissue to form roll-shaped pieces of tissue, and inserting the roll-shaped pieces of tissue in an axial direction into holes arrayed in a base block. Here, the tissue block is a paraffin-embedded tissue block or a frozen tissue block and may be any of tissue blocks insofar as it is capable of being sliced to obtain the aforementioned pieces of tissue. In addition, the sheet-like pieces of tissue may be those obtained by slicing the entire surface of the tissue block or those obtained by slicing only a part of diseased tissue contained in the tissue block.

According to the present invention, since the roll-shaped pieces of tissue fabricated by slicing the tissue block are used, the maximum length of the fabricated roll-shaped pieces of tissue can be made equal to the width of the tissue block. As a result, even when the thickness of the tissue block is small, it is possible to fabricate pieces of tissue having a sufficient length insofar as the width of the tissue block can be secured and to fabricate a considerable number of tissue array chips. Since the surface of the tissue block is sliced, the force required for the slicing step is smaller than that of the punching step concentrated at a single point, and the tissue block is little affected by tissue hardness. Since the pieces of tissue are collected in a small amount all over, the tissue block scarcely affects the utilization of the tissue block remaining after collecting the pieces of tissue.

It is preferred to further provide a step of cutting the roll-shaped pieces of tissue in an axial direction to have a predetermined length, which step is taken before or after the cutting step.

According to this invention, the tissue array block is fabricated either by inserting in the axial direction the roll-shaped pieces of tissue after being cut into a predetermined length into the holes of the base block or by cutting the roll-shaped pieces of tissue into a predetermined length after being inserted in the axial direction into the holes arrayed in the base block. Therefore, in each of these processes, the pieces of tissue arrayed in the tissue array block are brought to a state in which they have the predetermined length. In addition, it is also possible to insert roll-shaped pieces tissue only existing in the site of interests. Furthermore, it is possible to increase the number of tissue array chips to be fabricated relative to the amount of pieces of tissue collected from the tissue block in comparison with the case where cylindrical cores are collected by punching in order to embed pieces of tissue sliced in a small thickness.

A process of fabricating a tissue array sheet according to the present invention is characterized in that it includes the step of slicing the tissue array block fabricated by the process of fabricating a tissue array block in a direction in which the pieces of tissue inserted into the holes have a spiral shape in cross section.

According to the present invention, since the tissue array sheet is fabricated by slicing the tissue array block fabricated by the aforementioned process in the direction in which the pieces of tissue inserted into the holes have the spiral shape in cross section, the tissue or site of interests of the tissue array sheet to be fabricated suffer no defect even when slicing the tissue array block from any position. Since the spiral pieces of tissue arrayed in the tissue array sheet are collected from a region moving down through the surface of the tissue block in a coiling and rolling direction, they are to be collected from the regions very dispersed in comparison with the cores collected by punching from respective single points. When grasping the positional relationship between the pieces of tissue of the tissue array sheet and the tissue block, it is possible to specify the position of the tissue block from which the piece of tissue of the tissue array sheet has been collected. Furthermore, the positional relationship between the inside of the piece of tissue and the inside of the tissue block can be established.

A tissue array block of the present invention is characterized in that in the tissue array block having plural pieces of tissue retained on the base block, the pieces of tissue are roll-shaped.

According to this invention, since the roll-shaped pieces of tissue are used, it is possible to fabricate the same by slicing the tissue block even when the tissue block has a small thickness. By adjusting the length of the roll-shaped pieces of tissue, it is possible to make the lengths of the retained pieces of tissue equal to one another.

A tissue array chip of the present invention is characterized in that in the tissue array chip having plural pieces of tissue arrayed on the substrate, the pieces of tissue have a spiral (helical) shape.

According to this invention, the spiral (helical) pieces of tissue are to be collected from regions dispersed from respective starting points of spirals to respective terminal points thereof.

A system of fabricating a piece of tissue according to the present invention comprises means for slicing a tissue array block to obtain a sheet-like piece of tissue and means for coiling and rolling the sheet-like piece of tissue obtained by the slicing means to obtain a roll-shaped piece of tissue.

According to this invention, since the tissue block is sliced by the slicing means to form a sheet-like piece of tissue and since the sheet-like piece of tissue is coiled and rolled by the coiling and rolling means to form a roll-shaped piece of tissue, roll-shaped pieces of tissue can be fabricated from the tissue block.

A system of fabricating a tissue array block according to the present invention comprises means for slicing a tissue block to obtain roll-shaped pieces of tissue, means for cutting the roll-shaped pieces of tissue at predetermined positions and means for inserting the roll-shaped pieces of tissue in an axial direction into holes arrayed in a base block.

In the system of fabricating a tissue array block, the positions, at which the roll-shaped pieces of tissue are cut by the cutting means, can be set. For example, the position of cutting by the cutting means is set to be a position at which the roll-shaped pieces of tissue are cut in the axial direction in a predetermined length and, after the roll-shaped pieces of tissue are cut in the predetermined length by the cutting means, the pieces of tissue are inserted by the inserting means into the holes of the base block, thereby fabricating the tissue array block of the present invention. Otherwise, by using the cutting means to cut the roll-shaped pieces of tissue at first cutting positions and cut respective one ends of the pieces of tissue to align the respective one ends, using the inserting means to insert the roll-shaped pieces of tissue from the respective one ends into the holes and further using the cutting means to cut the inserted pieces of tissue at second positions in the predetermined length, the tissue array block of the present invention can be fabricated. The cutting positions may be controlled with a position sensor, by an action stored in advance in a microcomputer, or manually.

A system of fabricating a tissue array sheet according to the present invention comprises the aforementioned system of fabricating a tissue array block and means for slicing the tissue array block fabricated by the system of fabricating a tissue array block in a direction in which the pieces of tissue have a spiral shape in cross section.

According to this invention, since the tissue array block is fabricated by the aforementioned tissue array block-fabricating system and since the tissue array block can be sliced by the slicing means in the direction in which the pieces of tissue have a spiral (helix) shape in cross section, it is possible to fabricate a tissue array sheet having spirally shaped pieces of tissue arrayed.

Effects of the Invention

According to the process of the present invention for fabricating a piece of tissue, since the maximum length of pieces of tissue to be inserted into holes of the tissue block can be made equal to the width of the tissue block, insofar as the tissue block has a sufficiently large width, even when the thickness of the tissue block has a small thickness from the beginning or the thickness of the remaining tissue has been reduced during the course of the examination or analysis, it is possible to fabricate a considerable number of tissue array chips. Since the pieces of tissue are fabricated by the step of slicing the surface of the tissue block, the tissue block is little affected by tissue hardness in comparison with the punching step requiring a force concentrated at a single point. In comparison with the punching step requiring subtle adjustment of a force depending on the tissue hardness, a technique requiring a lot of skill is unnecessary to conduct, and the pieces of tissue can be fabricated by a comparatively simple operation.

In addition, according to the process of the present invention for fabricating a tissue array block, since the roll-shaped pieces of tissue are cut in a predetermined length, the lengths of the pieces of tissue arrayed on the tissue array block can be made equal. It is also possible to insert roll-shaped pieces of tissue composed only of the site of interests. Since the sheet-like pieces of tissue are embedded in a state of having been rolled, the number of tissue array chips to be fabricated relative to the amount of tissue collected from the tissue block can be increased in comparison with the conventional punching step.

According to the process of the present invention for fabricating a tissue array sheet, since the lengths of the pieces of tissue retained on the tissue block are made equal, even when the tissue array block is sliced from any position, the tissue or site of interests of the tissue array sheet does not suffer any defect. As a result, it is possible to prevent a situation constituting an obstacle to the examination or analysis and enhance the yield of the tissue array chips to be fabricated. Since the spiral pieces of tissue arrayed on the tissue array sheet are collected from the dispersed regions moving down through the surface of the tissue block in a coiling and rolling direction, the reliability of the examination or precision of the analysis is heightened. By grasping the positional relationship among the piece of tissue of the tissue array sheet, piece of tissue after being cut, piece of tissue before being cut and tissue block, it is possible to specify the position of the tissue block at which the piece of tissue has been cut. Furthermore, since it is possible to establish the positional relationship between the position inside the piece of tissue and the position inside the tissue block, when the site of interests has been found in one of the inside of the tissue block and the inside of the piece of tissue, the position of the site of interests in the other of the insides can be specified.

According to the tissue array block of the present invention, it is possible to fabricate a tissue array block using the sheet-like pieces of tissue obtained through slicing the tissue block. It is possible to fabricate a considerable number of tissue array chips using the tissue block even when the tissue block has a small thickness. By adjusting the lengths of the roll-shaped pieces of tissue, it is possible to make the lengths of the retained pieces of tissue equal, thereby fabricating tissue array chips having the piece of tissue or site of interests suffering no defect.

According to the tissue array chip of the present invention, the spiral pieces of tissue are to be collected from the dispersed regions corresponding to those from the starting point to the terminal point of the spiral. As a result, in comparison with the case where cores collected by punching from lop-sided regions are used, it is possible to heighten the reliability in a pathological test for examining the presence or absence of tumor cells etc. and to cover the heterogeneity of diseased tissue, thereby enabling the precision of analysis to be heightened.

According to the system of the present invention for fabricating a tissue array block, the roll-shaped pieces of tissue can be fabricated and inserted into the tissue block to make it possible to fabricate the tissue array block of the present invention. According to the system of the present invention for fabricating a tissue array sheet, it is possible to fabricate a tissue array sheet having spiral pieces of tissue arrayed. In addition, the tissue array chips of the present invention can be fabricated using the tissue array sheet.

BEST MODE FOR CARRYING OUT THE INVENTION

A piece of tissue-fabricating process P1, tissue array block-fabricating process P2 (P2-1 and P2-2), tissue array block B3, tissue array sheet-fabricating process P3 and tissue array chip C1 according to the present embodiment will be described hereinafter in detail. A tissue block B1 is a paraffin-embedded tissue block or frozen tissue block, for example, and is not limitative insofar as a block can be sliced into sheets. In the present embodiment, a description will be made using a tissue block B1 embedded in the neighborhood of the center of paraffin as an example. However, the same description will be applicable to the case using frozen tissue.

(Piece of Tissue-Fabricating Process)

First and second processes will be described herein below as the piece of tissue-fabricating process P1.

Figure 1:
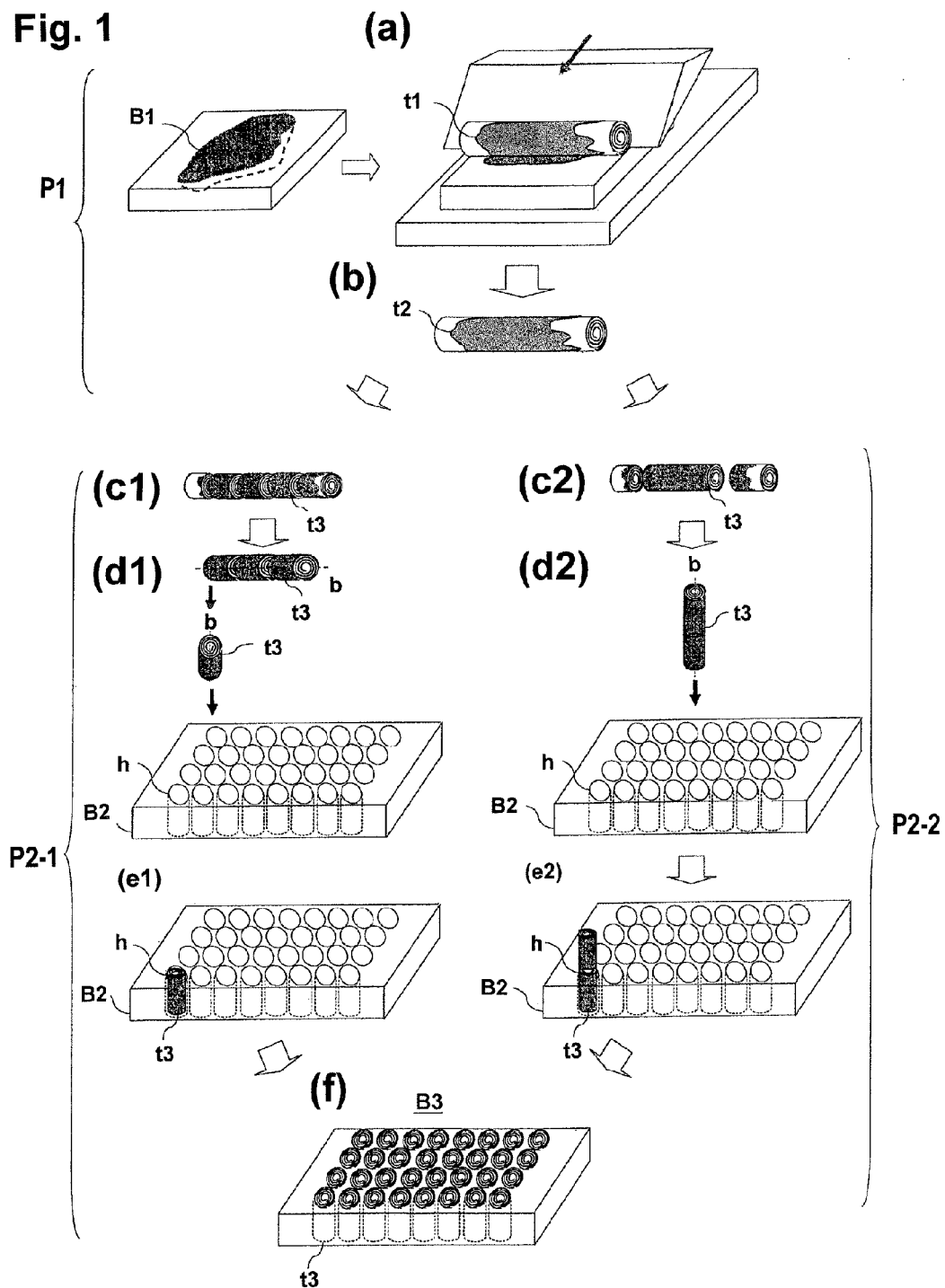
FIG. 1 includes explanatory views illustrating a process of fabricating pieces of tissue, a process of fabricating a tissue block and a tissue array block according to an embodiment of the present invention.

First Process:

In a slicing step, the tissue block B1 is sliced to fabricate a piece of tissue t2 having a sheet-like piece of tissue coiled and rolled into a roll shape (FIG. 1 (a) and (b)). To be specific, the surface of the tissue block B1 is sliced together with the surrounding paraffin using slicing means, such as a cutter. A portion of the tissue block sliced and substantially simultaneously formed into a sheet is coiled and rolled (FIG. 1(a)), with the front surface thereof as an inside surface, and upon completion of the slicing step, formed into a roll shape (FIG. 1(b)). It has heretofore been known that when a tissue block is sliced in a small thickness, the portion thereof sliced is sequentially curved, with the front surface as an inside surface and, when being continuously sliced as it is, is coiled and rolled into a roll shape. The present embodiment utilizes this feature. Though the piece of tissue t2 has a hollow core and assumes a substantially cylindrical shape, a step of densely coiling and rolling step may be added in order to heighten the integration degree of tissue. Incidentally, the roll shape used herein indicates a shape of the sheet-like piece of tissue t1 coiled, with one end thereof as an axis, and though the piece of tissue t2 preferably has a spiral (helical) cross section orthogonal to the axis thereof over the entire length thereof, it may have at least part thereof spiral in cross section.

In addition, the thickness of the piece of tissue T1 is not particularly limited insofar as the thickness is capable of coiling and rolling the piece of tissue as by desiccation into a roll shape. Generally, however, the thickness of the piece of tissue t1 is 200 μm or less (excluding 0 μm), preferably 30 μm to 200 μm, more preferably 50 μm to 100 μm. When the thickness is larger than 200 μm, the piece of tissue t1 induces a trace of crack to possibly mar the shape thereof, whereas when it is less than 30 μm, the piece of tissue t1 induces a defect when being sliced and, when having been formed into a tissue array chip, the user-friendliness in an examination is possibly hindered.

Second Process:

This is the same as the first process in the aspect that the tissue block B1 is sliced at the slicing step. However, whether a sheet of piece of tissue t1 to be obtained has a roll shape does not matter. The sheet-like piece of tissue t1 obtained at the slicing step is coiled and rolled into a roll shape at a forming step. For example, the roll-shaped piece of tissue t2 obtained at the slicing step of the first process may be stretched and then densely coiled and rolled into a roll shape. As a result, the integration degree of tissue can be heightened. In addition, a piece of tissue sliced in a thickness to an extent incapable of being coiled and rolled to assume a planar shape or a slightly curved shape may be formed into a roll shape.

According to the piece of tissue-fabricating process, a force required and an influence by tissue hardness are smaller in comparison with the case of punching requiring a force to be concentrated in a single point. The slicing means is seldom damaged by and seldom fails to slice a very hard tissue block, and does not necessitates considering a technique requiring a lot of skill as has been required in the punching step requiring the adjustment of a force depending on the hardness of the tissue block. Though the tissue block is used for various examinations and analyses after the pieces of tissue t1 are collected from it, since very thin sheet-like pieces of tissue t1 are collected from the surface of the tissue block B1 over all, there is little influence on the utilization of the tissue block from which the pieces of tissue have been collected, as compared with the case of the punching step of punching a single point in the width direction.

Furthermore, the roll-shaped piece of tissue t2 obtained by the piece of tissue-fabricating process has a maximum length in the direction of an axis b that becomes equal to the width of the tissue block B1. As a result, in the case where the tissue block B1 has a sufficient width even when it has a thin thickness, it is possible to obtain a piece of tissue t2 having a length capable of fabricating a considerable number of tissue array chips.

Incidentally, when a site of interests has been specified in the tissue block B1, a pre-step of inserting a cut into the tissue block B1 so as to surround the site of interests and a post-step of slicing may be performed to fabricate a piece of tissue t2 composed only of the site of interests. In addition, after the coiling and rolling step, it is preferred to heat the roll-shaped piece of tissue t2, thereby melting paraffin, and then cooling the piece of tissue to solidify the same. Consequently, a resultant piece of tissue t2 can be made stable in shape and becomes easy to handle.

(First Tissue Array Block-Fabricating Process)

The tissue array block-fabricating process P2 is divided into two. The first process P2-1 includes a cutting step ((c1) in FIG. 1) and an inserting step ((d1) in FIG. 1) as post-steps of the above piece of tissue-fabricating process P1.

At the cutting step, the roll-shaped piece of tissue t2 is cut in the direction of the axis b so as to have a predetermined length ((c1) in FIG. 1). The cutting position may be adjusted so that the piece of tissue t3 may have a desired length and site. Preferably, the length of the pieces of tissue t3 cut is made equal to or larger than the axial length of holes h arrayed in a base block B2 so that the pieces of tissue t3 may be filled in the holes h without any gap. When the piece of tissue t2 includes the site of interests, it may be cut to extract the site of interests. In this case, the site of interests on the surface of the tissue block B1 is first specified and the piece of tissue t2 is then cut so as to extract a site corresponding to the specified site of interests.

At the inserting step, the pieces of tissue t3 cut in the predetermined length are inserted into the holes h arrayed in the base block B2 ((d1) in FIG. 1). The base block B2 is a block having plural cylindrical holes h arrayed therein. These holes h are formed as by punching at a separate step. The base block B2 may be formed of a material having a surface sliceable into a sheet and, for example, is a paraffin block. The pieces of tissue t3 obtained from different tissue blocks B1 or the same tissue block B1 may be inserted into the holes h, respectively.

(Second Tissue Array Block-Fabricating Process)

The second process P2-2 includes, as post-steps of the piece of tissue-fabricating process P1, a pre-step ((c2) in FIG. 1), a subsequent inserting step ((d2) in FIG. 1) and a cutting step ((e2) in FIG. 1. Only points of the second process different from the first tissue array block-fabricating process will be described hereinafter. At the pre-step, the pieces of tissue t3 are inserted in the direction of the axis b into the holes h of the base block B2 ((d2) in FIG. 1). At the subsequent cutting step, the pieces of tissue t3 inserted into the holes h are cut in the direction of the axis b to have the predetermined length ((e2) in FIG. 1). The cutting position is set to be the front surface position of the base block B2, and the pieces of tissue t3 cut are preferably filled in the holes h.

In either of the fabricating processes, after the pieces of tissue t3 are inserted into the base block B2, they are preferably fixed to the base block B2. With the pieces of tissue t3 inserted into the holes h, for example, a step of heating the base block B2 to dissolve paraffin or filling a paraffin melt into the holes h and a subsequent step of solidifying the paraffin are taken.

(Tissue Array Block)

A tissue array block B3 is fabricated by the first tissue array block-fabricating process or the second tissue array block-fabricating process (FIG. 1(f)). The tissue array block B3 has the roll-shaped pieces of tissue t3, which are obtained by coiling and rolling the sheet-like pieces of tissue, retained in the holes h, . . . , h arrayed in the base block B2. Since the pieces of tissue t3 are cut to the predetermined length at the cutting step, the pieces of tissue t3 arrayed in the tissue array block B3 are adjusted to have an equal length. The case where the pieces of tissue t3 are cut in a length equal to or larger than the depth of the holes h is further preferred because the pieces of tissue t3 are filled in the holes h. In addition, since the very thin sheet-like pieces of tissue t1 are embedded in the form of the roll shape, it is possible to increase the number of tissue array chips C1 produced relative to the amount of the pieces of tissue collected from the tissue block B1 in comparison with the case where cylindrical cores are collected by punching.

(Tissue Array Sheet-Fabricating Process)

Figure 2:
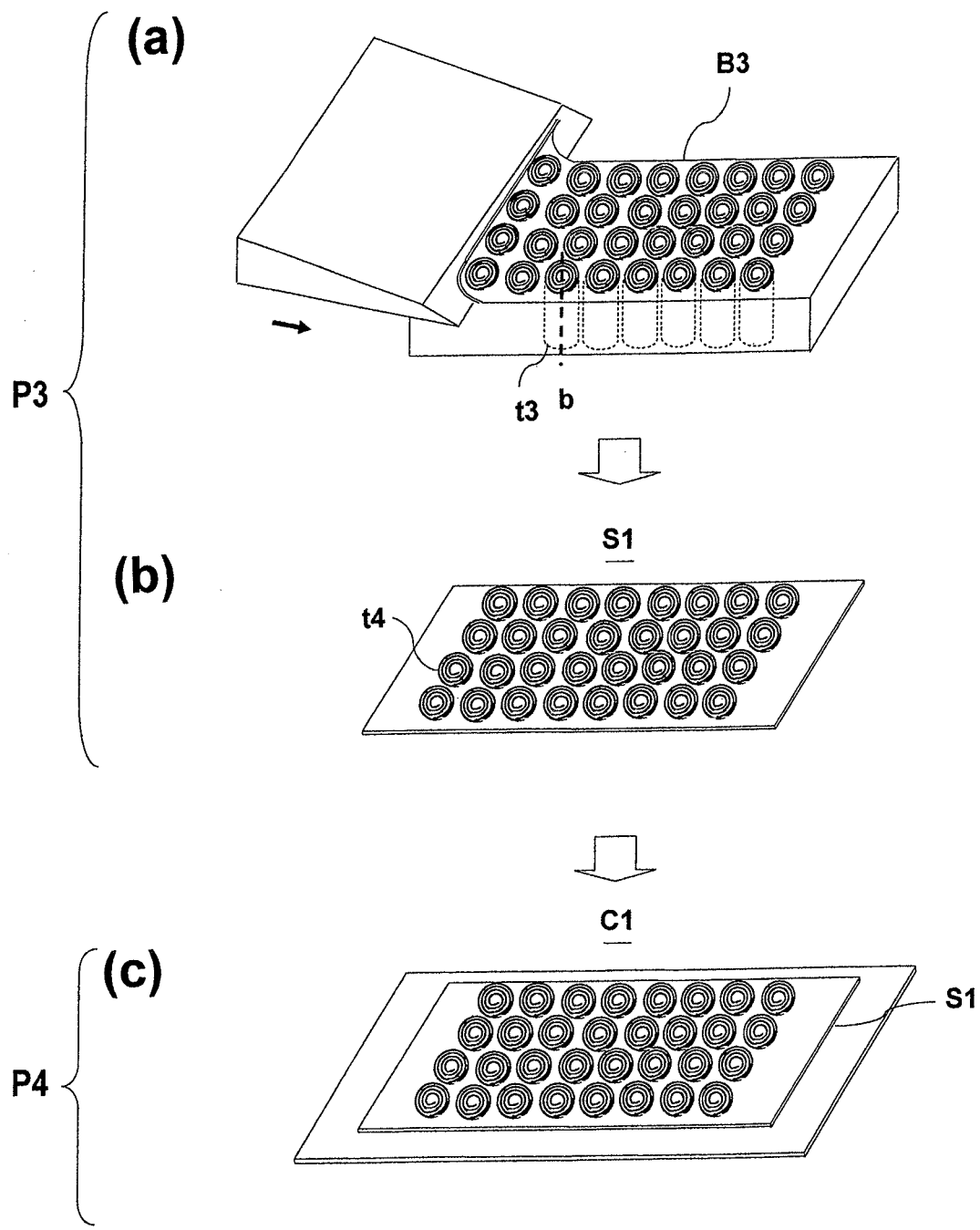
FIG. 2 includes explanatory views illustrating a process of fabricating a tissue array sheet according to the present embodiment.

FIG. 2 includes explanatory views illustrating a tissue array sheet-fabricating process P3 and a tissue array chip-fabricating process P4 of the present embodiment. The array sheet-fabricating process P3 includes, as a post-step of the tissue array block-fabricating process, a tissue array block-slicing step (FIG. 2(a)).

At the tissue array block-slicing step, the tissue array block B3 fabricated by the tissue array block-fabricating process P2-1 or P2-2 is sliced in a direction in which the pieces of tissue t3 are spiral (helical) in cross section, i.e. in a direction intersecting the axis b of the pieces of tissue t3 (FIG. 2(a)). As a result, a tissue array sheet S1 having plural spiral (helical) pieces of tissue t4 arrayed thereon is fabricated (FIG. 2(b)).

A tissue array chip-fabricating process P4 includes a step of mounting the tissue array sheet S1 on a substrate of a glass slide or nylon film (FIG. 2(c)). As a result, a tissue array chip C1 having the spiral pieces of tissue t4 arrayed thereon is fabricated.

Figure 3:
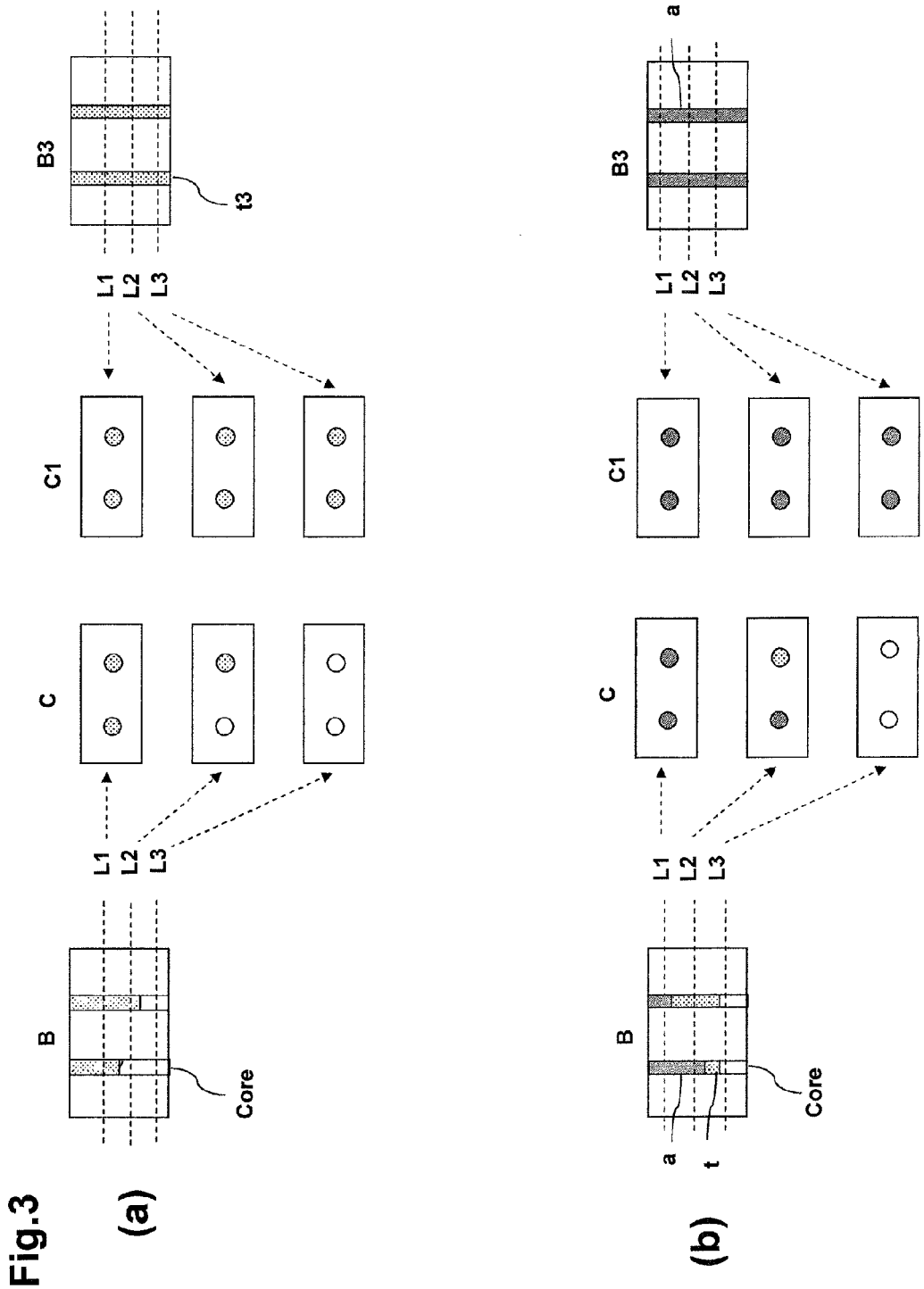
FIG. 3 includes explanatory views illustrating the difference between a conventional tissue array chip and a tissue array chip according to the present embodiment.

FIG. 3(a) is an explanatory view illustrating the comparison between the state in which tissue array chips C have been fabricated by the conventional punching step from a tissue array block B and the state in which tissue array chips C1 have been fabricated from the tissue array block B3 of the present embodiment, and (b) an explanatory view illustrating the comparison between the states in which the tissue array chips C and C1 composed of sites of interests a have been fabricated respectively from the tissue array blocks B and B3 In the conventional tissue array block B, the portions of tissue t and sites of interests a contained in the cores have different lengths, there are defects of the pieces of tissue or sites of interests in the tissue array chip C depending on positions L1 to L3 at which the slicing step is taken. In the tissue array block B3 of the present embodiment, since the lengths of the pieces of tissue t3 or sites of interests a are made equal, there is no defect of the pieces of tissue or sites of interests in the tissue array chip C1 even when the slicing step is taken at any of the positions L1 to L3.

Figure 4:
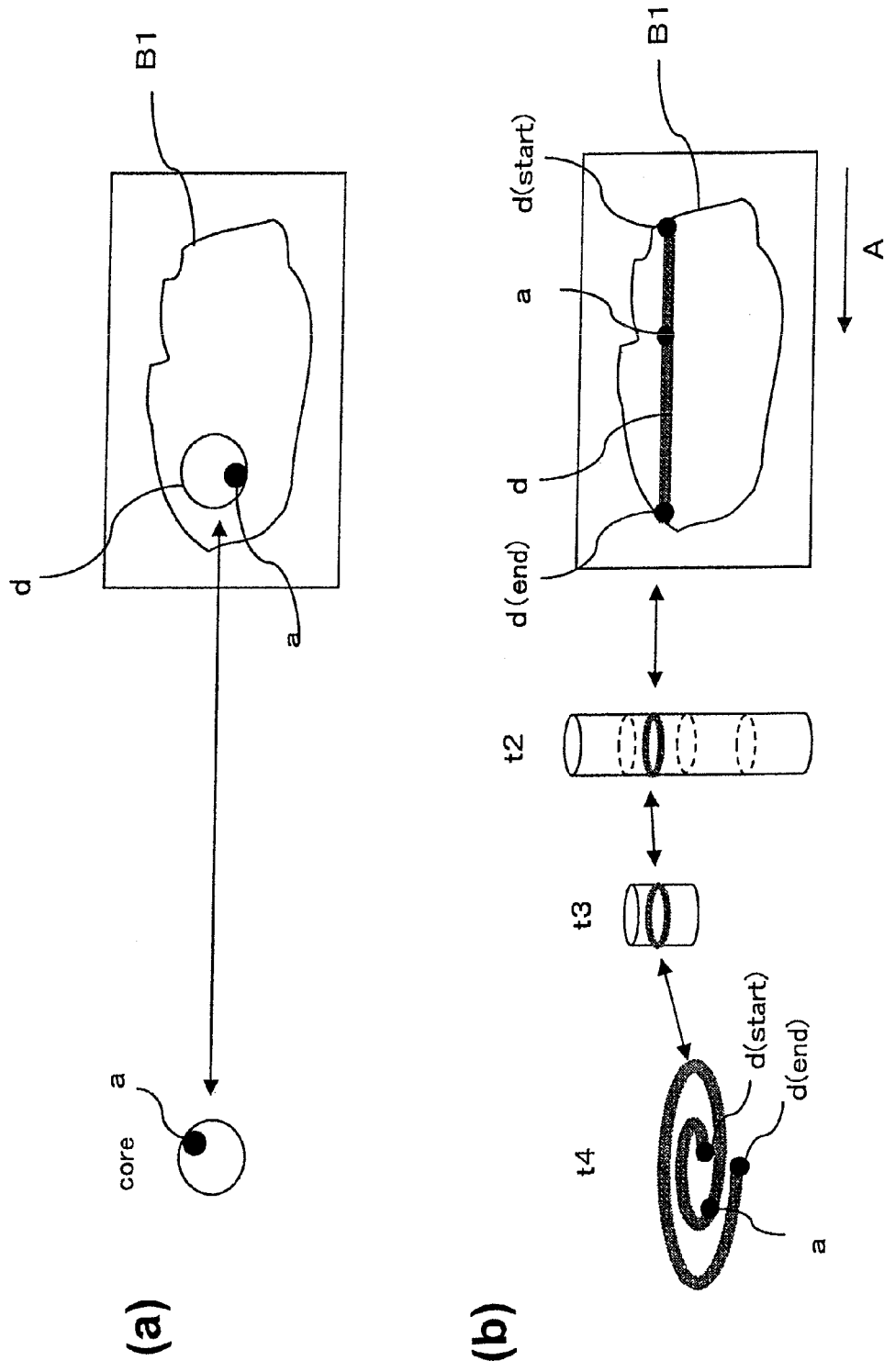
FIG. 4 includes explanatory views illustrating the difference between the conventional tissue array chip and the tissue array chip according to the present embodiment.

FIG. 4(a) is a diagram illustrating the positional relationship between a core on the tissue array chip C and a collection region d of the tissue block B1 according to the conventional punching step, and (b) a diagram showing the positional relationship between a spiral piece of tissue t4 on the tissue array chip C1 and a collection region d of the tissue block according to the present embodiment. In the case of the conventional punching step, the core is collected from the very lopsided region d. On the other hand, since the spiral piece of tissue t4 is collected from the dispersed region d transecting the tissue block B1, it is possible to heighten the reliability in an examination or the precision of analysis in comparison with the conventional technique of single-point punching.

In addition, according to the conventional punching step, as shown in FIG. 4(a), the positional relationship between the inside position of the core and the inside position of the collecting region d of the tissue block B1 is unclear. For this reason, even when the site of interests a exists in the core, for example, it is difficult to specify where the site of interests a is positioned in the tissue block B1. On the other hand, according to the present embodiment, as shown in FIG. 4(b), the positional relationship among the piece of tissue t4 on the tissue array chip, the piece of tissue t3 after the cutting step, the piece of tissue t2 before the cutting step and the tissue block B1 is grasped. An arrow A in the figure indicates the coiling and rolling direction at the roll-forming step, and the inside end d (start) of the piece of tissue t4 is on the coiling and rolling starting side and the outside end d (end) thereof is on the coiling and rolling terminating side. By grasping the positional relationship, it is possible to establish the positional relationship between the inside position of the piece of tissue t4 and the inside position of the tissue block B1.

Embodiment

An examination of the presence or absence of a site of interests in diseased tissue is performed in the following manner. A tissue array chip C1 is fabricated by any of the processes described above using a tissue block B1 constituting a test object. Since a piece of tissue t4 contained in the tissue block B1 is collected from a dispersed region from one end to the other end of the tissue block, the reliability in the examination can be heightened in comparison with the prior art using the single-point punching step. When a site of interests has been found in a piece of tissue t4 contained in the tissue array chip C1, by causing the piece of tissue t4 and tissue block B1 to correspond in position to each other, it is possible to specify the position of the site of interests in the tissue block B1.

Furthermore, when it is desired that the site of interests, such as diseased tissue, that has already been found in the tissue block B1 be included in the tissue array chip C1, the following procedure is performed. A pretreatment comprises using the piece of tissue obtained by slicing the surface of the tissue block B1 to fabricate a tissue chip and staining the site of interests to specify the position thereof. Next, the tissue chip and tissue block B1 are contrasted with each other to specify a region corresponding to the site of interests in the tissue block B1, and a cut is inserted so as to surround the specified region. The tissue block-slicing step and roll-forming step are then taken to fabricate a roll-shaped piece of tissue t2. The piece of tissue t2 is composed only of the site of interests. The cutting step and inserting step are taken using the piece of tissue t2 to fabricate a tissue array block B3. Since the tissue array block B3 has filled therein a piece of tissue t3 composed of the site of interests, it is possible to prevent a defect of the site of interests when fabricating a tissue array chip C1. It is also possible to cause the inside position of the site of interests in the tissue block B1 to correspond to the inside position of a piece of tissue t4. Since the site of interests is collected from the dispersed region, the heterogeneity thereof is covered to enhance the degree of analysis. Incidentally, when the pieces of tissue t2 have been fabricated from the entire surface of the tissue block, in cutting the piece of tissue t3 at the cutting step, the procedure thereof may comprise causing the tissue chip and roll-shaped piece of tissue 12 at the pretreatment to correspond to each other and cutting the piece of tissue t2 so as to extract a site corresponding to the site of interests.

(Piece of Tissue-Fabricating System)

Figure 5:
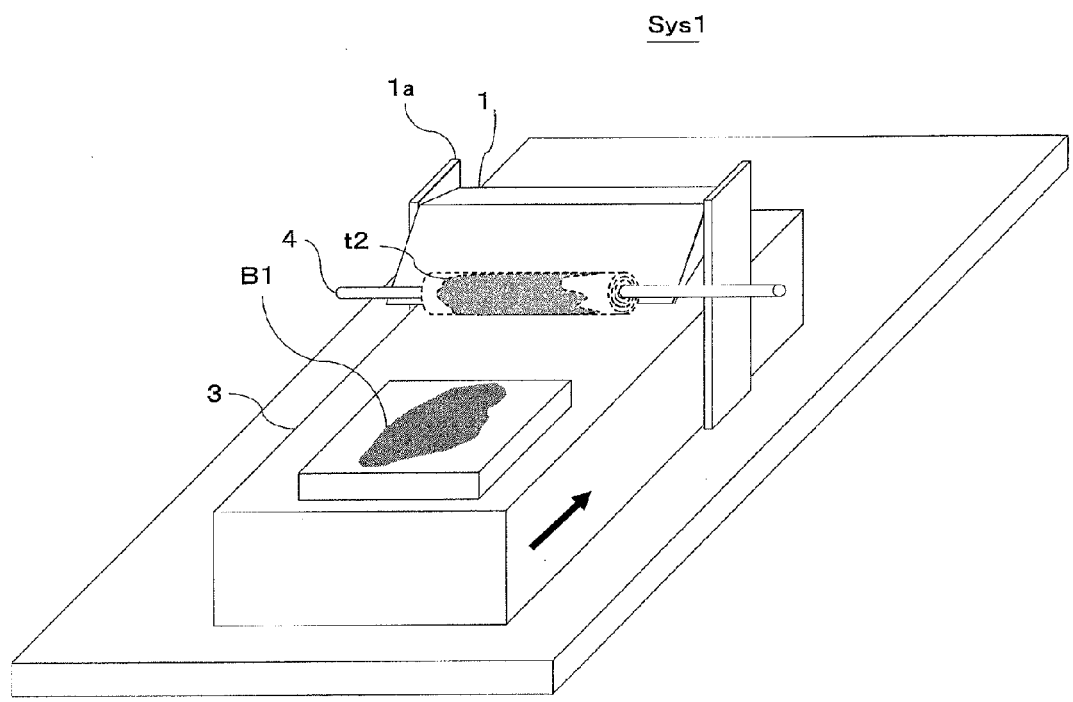
FIG. 5 is an explanatory view illustrating a system of fabricating a piece of tissue according to the present embodiment.

FIG. 5 is an explanatory view illustrating a piece of tissue-fabricating system Sys 1 according to the present embodiment. The piece of tissue-fabricating system Sys 1 is suitable for fabricating the roll-shaped piece of tissue t2. The piece of tissue-fabricating system Sys 1 is provided with at least slicing means 1.

The slicing means 1 has a function to slice the surface of the tissue block B1 to fabricate the roll-shaped piece of tissue t1 and is a cutter, for example. The slicing means 1 is configured so that the surface of the tissue block B1 may be sliced in a desired thickness in accordance with a relative change in position of the tissue block B1. In the present embodiment, the slicing means 1 is attached and fixed to a fixing member 1a and, by adjusting the fixing position or fixing angle, it is possible to adjust the thickness of the roll-shaped piece of tissue t1. In addition, the tissue block B1 is mounted on conveying means 3 for conveying the tissue block B1 and, by sliding the tissue block B1 relative to the slicing means 1, the surface of the tissue block B1 is sliced. Incidentally, the slicing means 1 may be slid, with the tissue block B1 fixed.

In the present embodiment, since a paraffin-embedded tissue block is used as the tissue block B1, when the tissue block B1 is sliced with the slicing means 1, the sheet-like piece of tissue t1 is coiled and rolled, with the front surface thereof as an inside surface. A rod-shaped guide member 4 is disposed in the vicinity of the slice means 1 and along the axial direction of the slice means 1, and the sheet-like piece of tissue formed by slicing is allowed to sequentially twine around the guide member 4. Incidentally, the guide member 4 is fixed with a fixing member not shown so as to make the relative position thereof constant relative to the slice means 1.

Furthermore, roll-forming means may be further provided for densely coiling and rolling the piece of tissue t1. The roll-forming means is materialized, for example, through making it possible to rotate the guide member 4 and adjust the temperature of the guide member. The piece of tissue t1 is adhered to the guide member 4 by elevating the temperature of the guide member upon the end of the sheet-like piece of tissue t1 coming into contact with the guide member to dissolve paraffin and then lowering the temperature to solidify the paraffin and, in that state, the guide member 4 is rotated to densely coil and roll the piece of tissue t1. It may be adopted to adjust the temperature during the course of coiling and rolling and make the hardness of the piece of tissue t1 easy to form. It may also be adopted to elevate and lower the temperature of the guide member again at the time of the completion of coiling and rolling to dissolve and solidify the contained paraffin, thereby making the roll shape stable.

Figure 6:
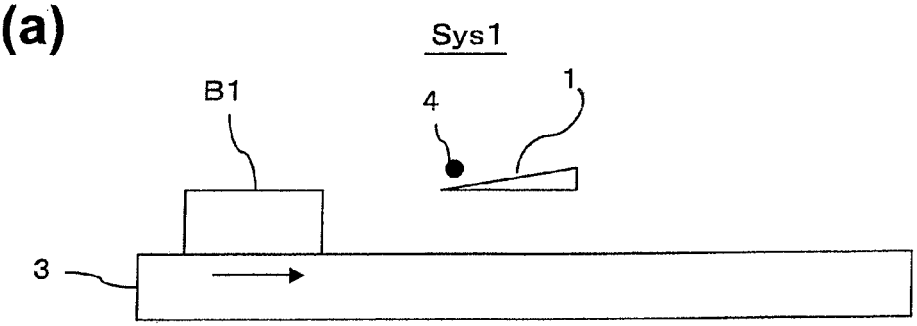
FIG. 6 includes explanatory views illustrating the operation of the system of fabricating the piece of tissue according to the present embodiment.
Figure 6:
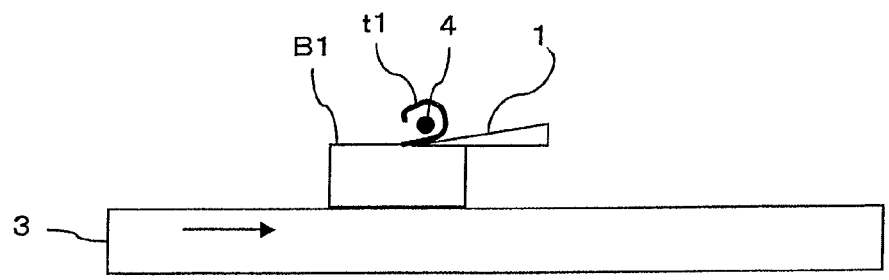
Figure 6:
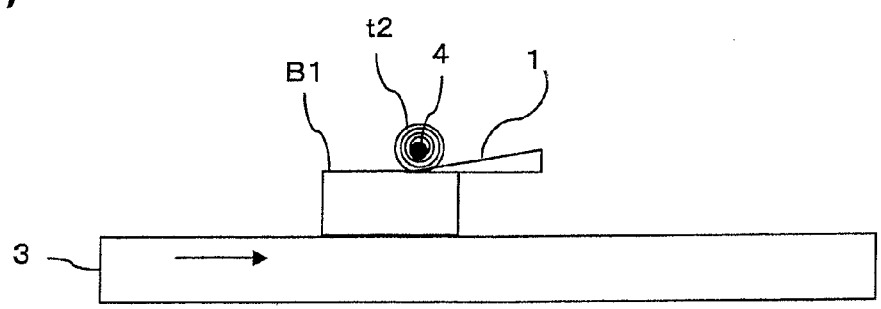

FIG. 6 includes explanatory view illustrating the movement of the piece of tissue-fabricating system Sys 1. The conveying means 3 conveys the tissue block mounted thereon to the side of the slicing means 1 (FIG. 6(a)). The slicing means 1 slices the conveyed tissue block B1 to fabricate the sheet-like piece of tissue t1 (FIG. 6(b)). The slicing means 1 causes the fabricated piece of tissue t1 to sequentially twine around the guide member 4 to fabricate the roll-shaped piece of tissue t2, with the guide member 4 as an axis (FIG. 6(c)). Thereafter, the piece of tissue may be densely coiled and rolled.

(Tissue Array Block-Fabricating System)

Figure 7:
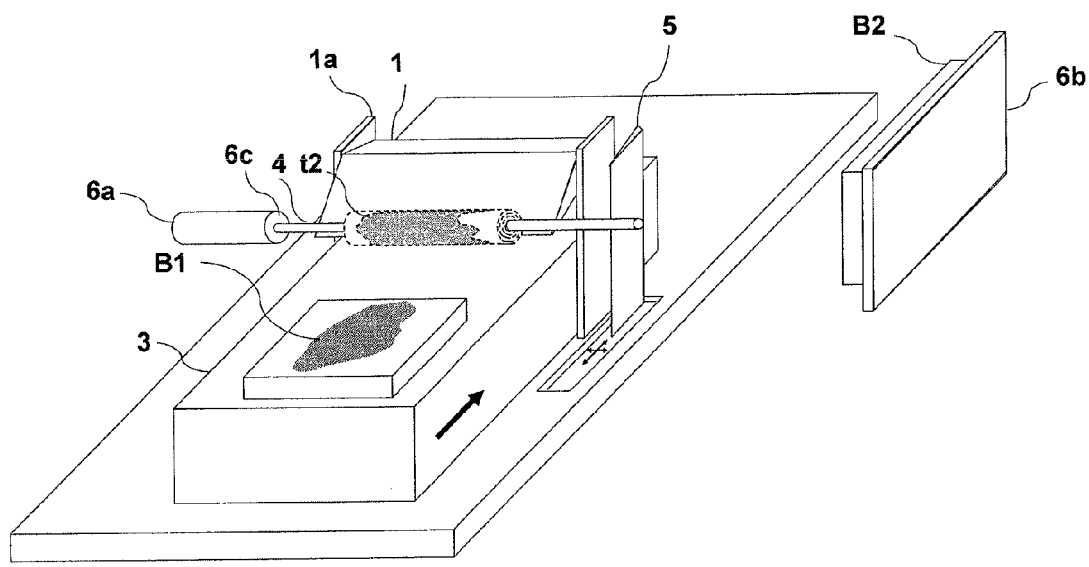
FIG. 7 is an explanatory view illustrating a system of fabricating a tissue array block according to the present embodiment.

FIG. 7 is an explanatory view illustrating a tissue array block-fabricating system Sys 2 according to the present embodiment. The tissue array block-fabricating system Sys 2 includes cutting means 5 and inserting means 6 in addition to the means in the piece of tissue-fabricating system Sys 1.

The cutting means 5 has a function to cut the roll-shaped piece of tissue t2 at a set position. For example, the cutting means 5 is a cutter having a cutting edge on the side of the guide member 4. The guide member 4 slides in a direction intersecting the axial direction of the guide member 4 so as to be movable in the axial direction of the guide member 4 and can be controlled in position based on information or a program from a sensor.

The inserting means 6 has a function to insert the roll-shaped pieces of tissue t2 in the axial direction into the holes h arrayed on the base block B2. For example, the inserting means 6 comprises slide means 6a for sliding along the guide member 4 the roll-shaped pieces of tissue t2 coiled and rolled on the guide member 4 and positioning means 6b for retaining the base block B2 and positioning the same in three directions. The slide means 6a is a cylindrical member into which the guide member 4 is inserted and can be controlled so as to slide to a predetermined position along the guide member 4. The positioning means 6b can fix the base block B2 to a surface on the side of the guide member 4 and has a function to position the base block B2 in the X-, Y- and Z-directions based on the information or program from the sensor.

Figure 8:
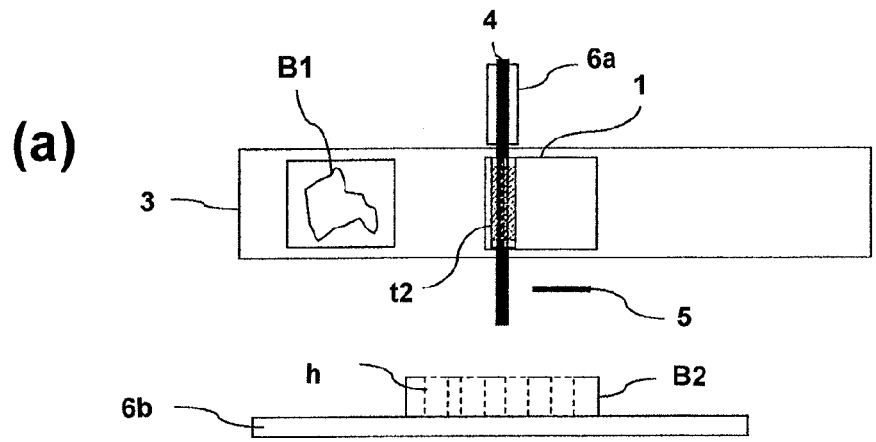
FIG. 8 includes explanatory views illustrating the operation of the system of fabricating the tissue array block according to the present embodiment.
Figure 8:
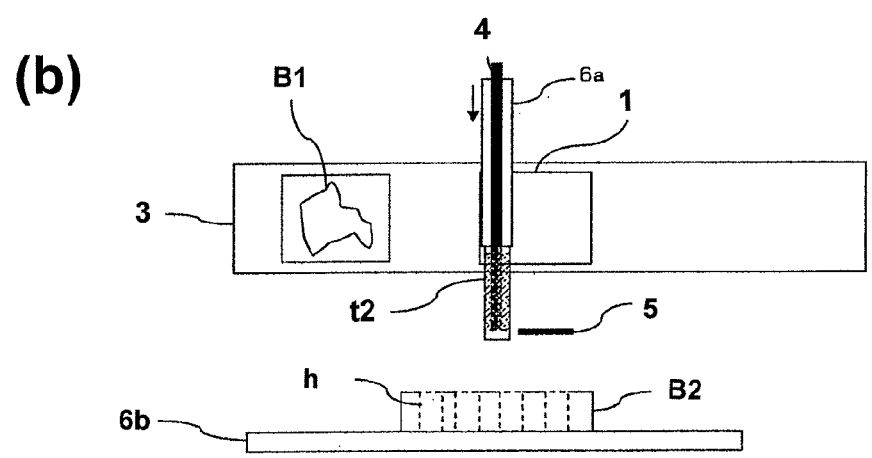
Figure 8:
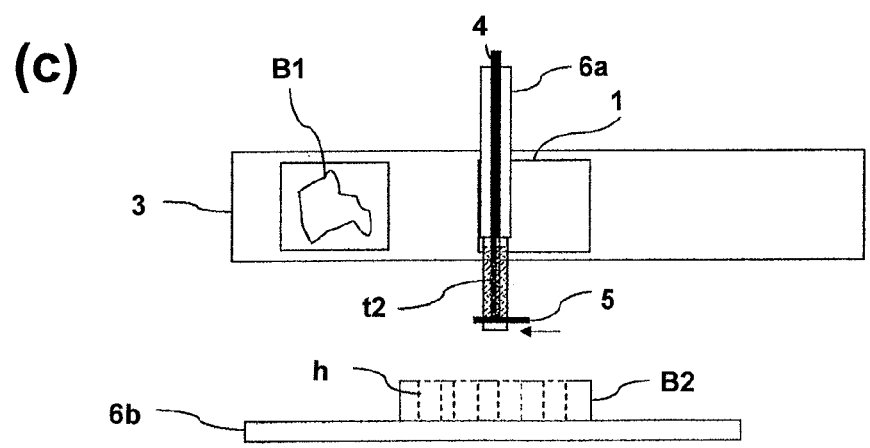
Figure 8:
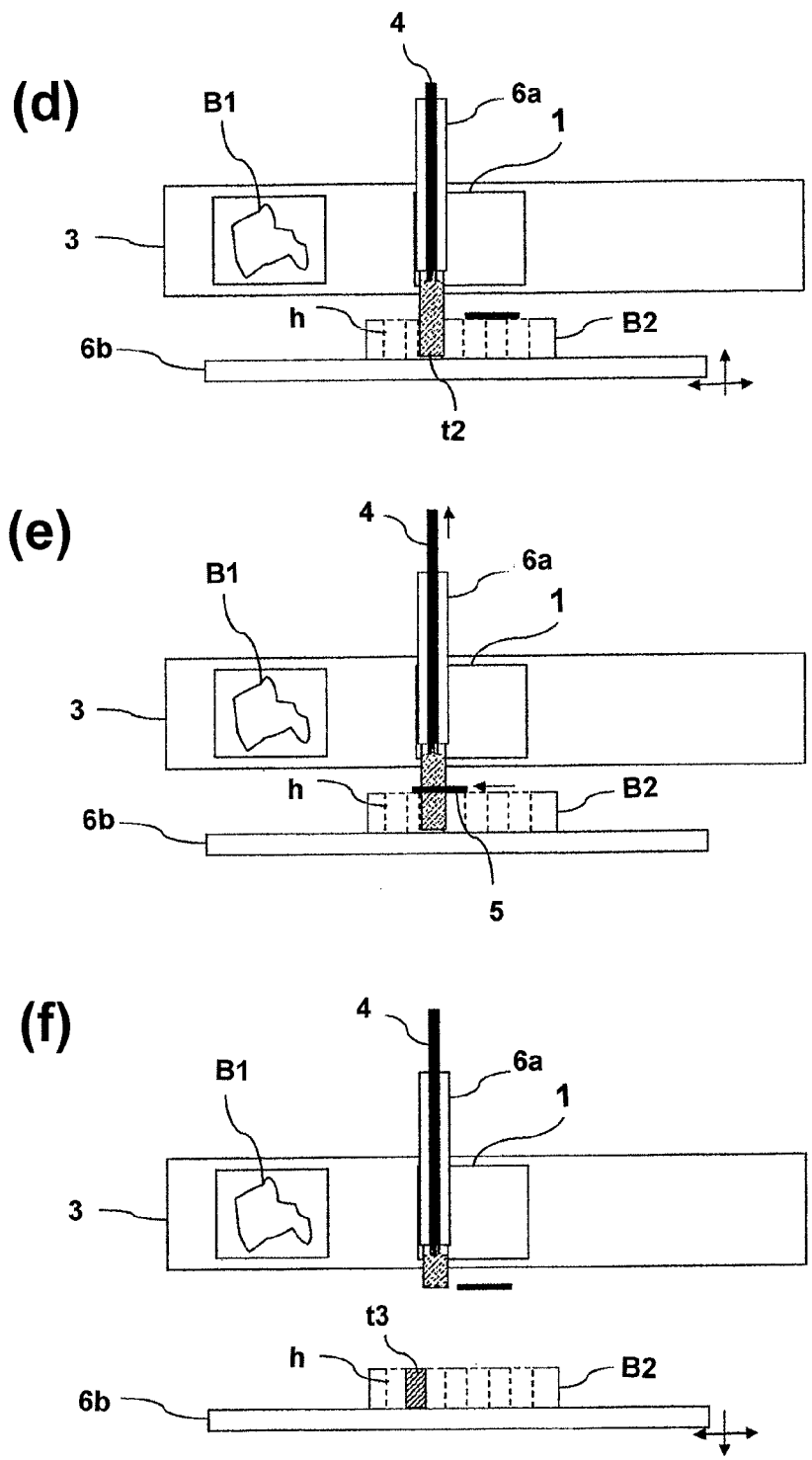

FIG. 8 includes explanatory views illustrating how the tissue array block-fabricating system Sys 2 moves. As a consequence of the fabrication of the piece of tissue by the tissue array block-fabricating system, the piece of tissue t2 is brought to a state in which it has been coiled and rolled on the guide member 4 (FIG. 8(a)). The sliding means 6a slides along the guide member 4 to move the piece of tissue t2 to a set position by means of a surface 6c in contact with the piece of tissue t2 (FIG. 8(b)). The set position is a position at which a paraffin portion at the end of the piece of tissue t2 projects from the distal end of the guide member 4. The cutting means 5 is positioned and then slid to cut the projecting portion of the piece of tissue t2 (FIG. 8(c)). As a result, the paraffin portions are cut off to align the ends of the pieces of tissue t2. Next, the positioning means 6b causes a desirable hole h to face the guide member 4 and moves in the direction of the guide member 4 to insert the piece of tissue t2 into the desirable hole h (FIG. 8(d)). After pulling the guide means 4 out of the hole h, the cutting means 5 is slid to cut the piece of tissue t2 (FIG. 8(e)). As a result, a state is obtained in which the cut piece of tissue t3 is inserted into the hole h (FIG. 8(f)).

Incidentally, in the case where pieces of tissue collected from different tissue blocks B1 are inserted into holes h, . . . , h, plural tissue array block-fabricating systems Sys 2 are disposed in parallel, and a single positioning means 6b is prepared for the tissue array block-fabricating systems Sys 2. The positioning means 6b is used to position the base blocks B2 relative to the tissue array block-fabricating systems Sys 2, thereby causing the tissue array block-fabricating systems Sys 2 to function in the same manner as described above.

In addition, though the tissue array block-fabricating system Sys 2 is for realizing the second tissue array block-fabricating process, is may be used as a system for realizing the first tissue array block-fabricating process. In this case, the system is further provided with grasping means for grasping the piece of tissue t3 cut by the cutting means 5 and, after the piece of tissue t2 is cut by the cutting means in a predetermined length, the cut piece of tissue grasped by the grasping means is to be inserted into the base block B2. Furthermore, in the present embodiment, a separate punching mechanism is used to form holes h in the base block B2, and the positioning means 6b is used to position the holes h and the pieces of tissue t2. However, by providing the system Sys 2 coaxially with the punching means and the guide member, forming the holes h in the base block B2 by the punching means and then inserting the pieces of tissue t3 at the forming positions into the holes by the inserting means, the positioning step may be simplified.

In addition, the tissue array block-fabricating system Sys 2 is preferably provided with fixing means for fixing the pieces of tissue t3 having been inserted into the holes h to the base block B2. The fixing means has a function to heat and cool the base block B2, with the pieces of tissue t3 inserted into the holes, or a function to fill and solidify molten paraffin, for example. For example, the positioning means 6b is provided with a temperature adjusting function to adjust the temperature in a state wherein the base block B2 is retained so as to bring the positioning means into contact with one surface of the base block B2, thereby heating and cooling the base block B2.

(Tissue Array Sheet-Fabricating System Sys 3)

Figure 9:
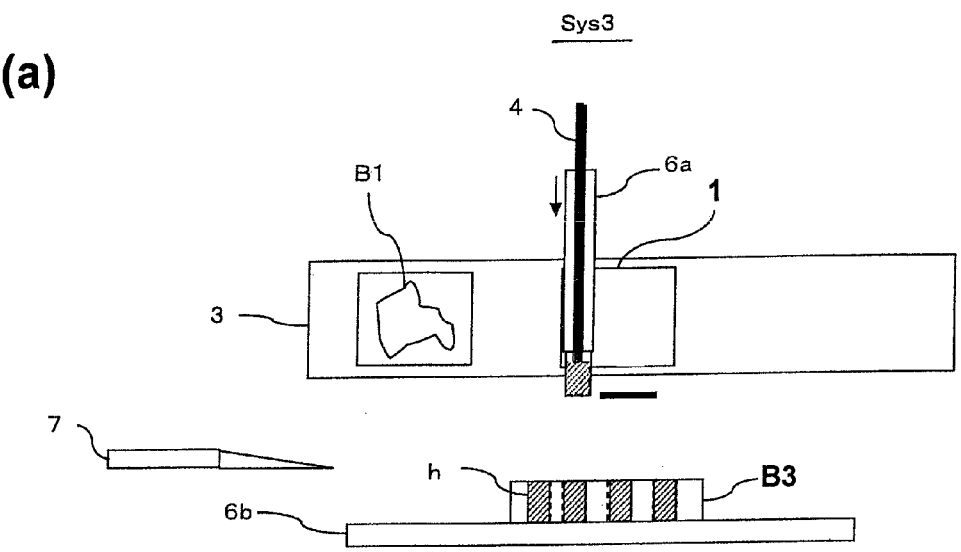
FIG. 9 includes explanatory views functionally illustrating a system of fabricating a tissue array sheet according to the present embodiment.
Figure 9:
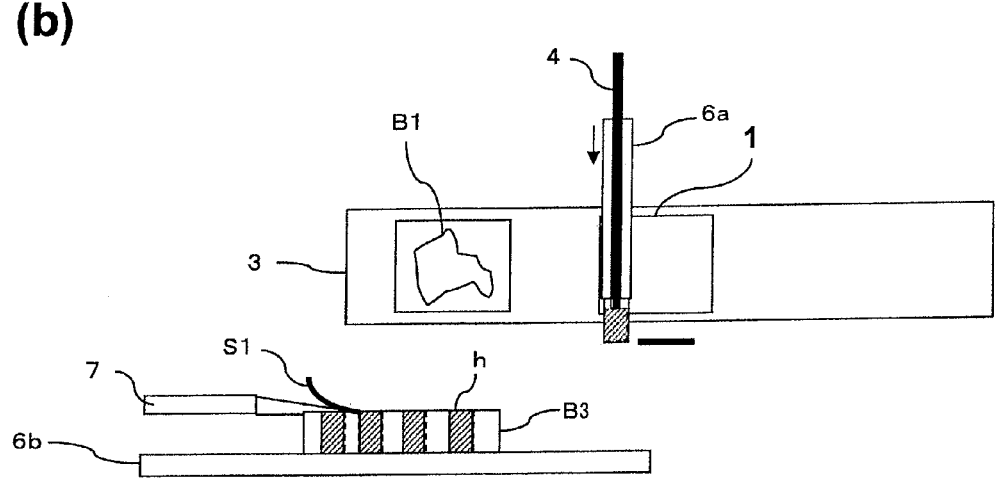
Figure 9:
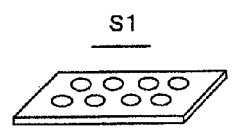

A tissue array sheet-fabricating system Sys 3 is provided with slicing means 7 for slicing the tissue array block B3 in addition to the means of the tissue array block-fabricating system 2. FIG. 9 includes explanatory views functionally illustrating the tissue array sheet-fabricating system Sys 3.

The slicing means has a function to slice the tissue array block B3 in the direction in which the pieces of tissue t3 having been inserted into the holes have a spiral shape in cross section. The slicing means 7 is a cutter, for example, having a cutting edge of a width substantially the same as the width of the tissue array block B3. The position or angle at which the slicing means comes into contact with the tissue array block B3 is adjustable and, by adjusting it, it is possible to adjust the thickness of the tissue array sheet t4.

Upon completion of the fabrication of the tissue array block by the tissue array block-fabricating system sys 2, the tissue array block B3 is in a state in which it has been mounted on the positioning means 6b (FIG. 9(a)). By positioning the pieces of tissue t3 in the tissue array block B3 by the positioning means 7 so as to bring the surfaces of the pieces of tissue arrayed into contact with the slicing means 7 and sliding the sliding means to the side of the slicing means 7, the surfaces of the pieces of tissue t3 arrayed on the tissue array block B3 are sliced (FIG. 9(b). As a result, it is possible to fabricate a tissue array sheet S1 (FIG. 9(c)). Then, by mounting the tissue array sheet S1 on a substrate, a tissue array chip C1 is fabricated.

Example

The fabricating method of the above embodiment was performed to fabricate a tissue array chip. The tissue used was mesothelial tumor tissue and was embedded in paraffin to fabricate a paraffin-embedded tissue block that was used as a tissue block. In addition, a paraffin block was formed therein with holes h to use the resultant block as a base block.

(Slicing step and roll-forming step) A tissue block was sliced by a cutter to fabricate a sheet-like piece of tissue t1 and, at the same time, the piece of tissue t1 was coiled and rolled to fabricate a roll-shaped piece of tissue t2. The thickness of the sheet-like piece of tissue t1 was set to be about 50 to 100 µm in view of the easiness of formation and observation, and the diameter of the roll-shaped piece of tissue t2 was set to be about 1 mm to 2.5 mm from the standpoint of the integration degree in the tissue array chip. (Cutting step) The roll-shaped piece of tissue t2 was cut in a length equal to the depth of the holes to fabricate a piece of tissue t3. (Inserting step) The cut piece of tissue t3 was inserted into the hole of the tissue block. This step was repeated using different tissue blocks to fabricate a tissue array block having plural pieces of tissue t3 collected from the different tissue blocks. The tissue array block was mounted on a glass slide to form tissue array chip that was then subjected to immunostaining.

Figure 10:
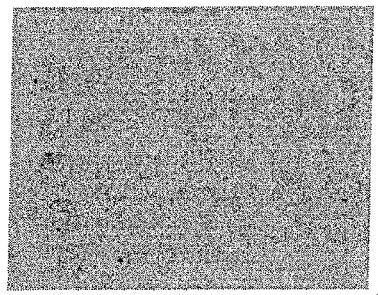
FIG. 10 includes photographs illustrating the difference between the tissue array chip according to the present embodiment and the conventional tissue array chip.
Figure 10:
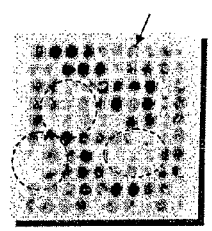
Figure 10:
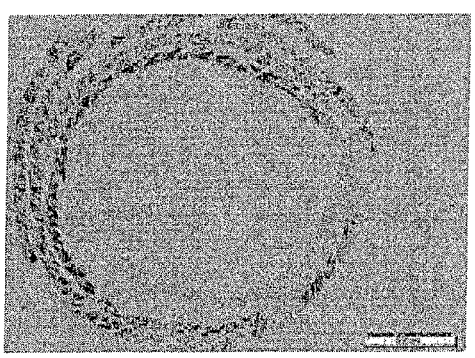
Figure 10:
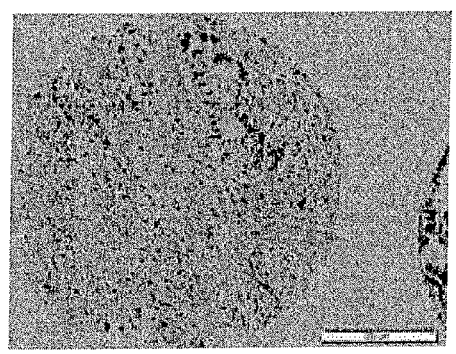
Figure 10:
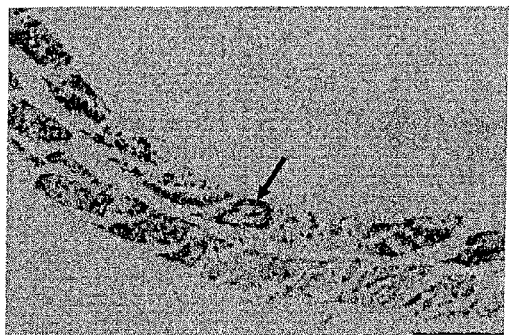
Figure 11:
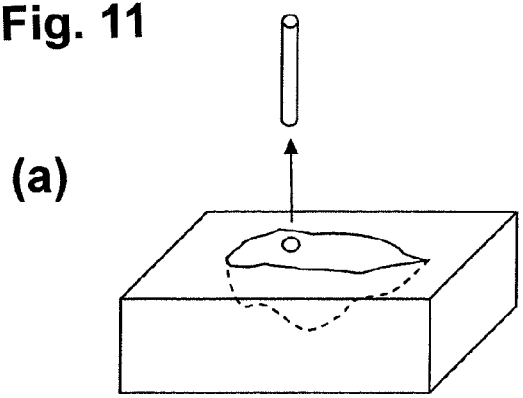
FIG. 11 includes explanatory views illustrating a process of fabricating the conventional array chip.
Figure 11:
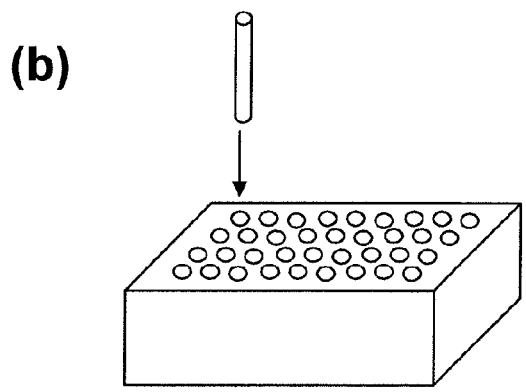
Figure 11:
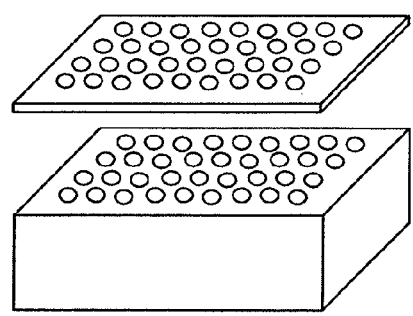
Figure 11:
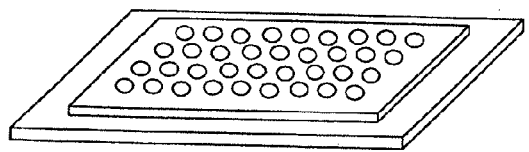
Figure 12:
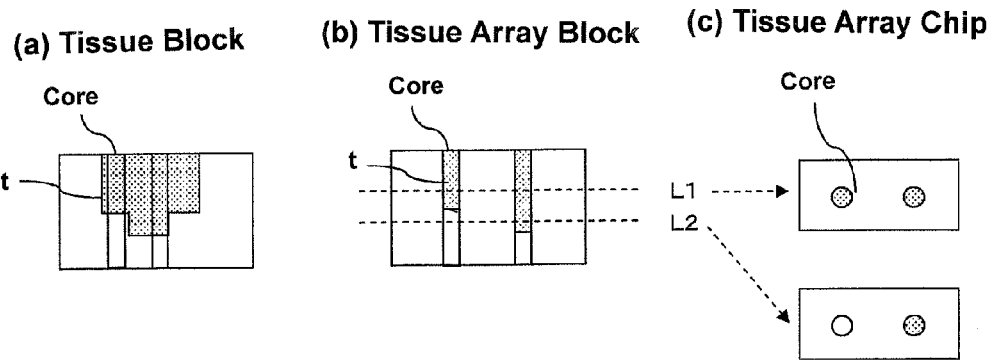
FIG. 12 includes explanatory views illustrating a conventional tissue block, a conventional tissue array block and conventional tissue array chips.
Figure 13:
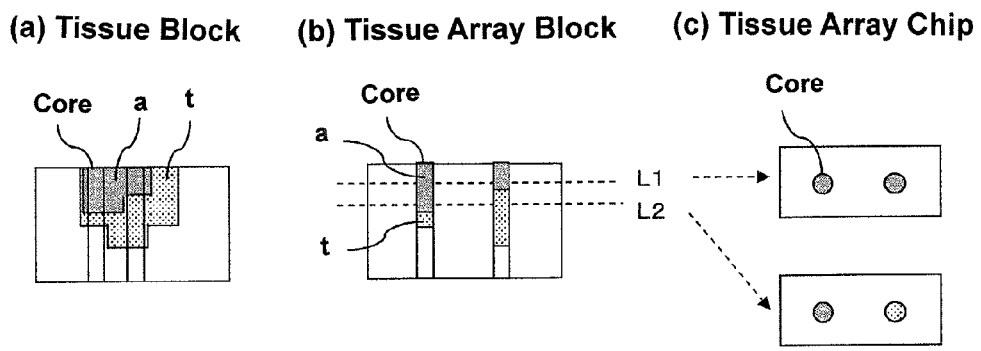
FIG. 13 includes explanatory views illustrating a conventional tissue block, a conventional tissue array block and conventional tissue array chips assumed when a conventional site of interests has been used as a target.
Figure 14:
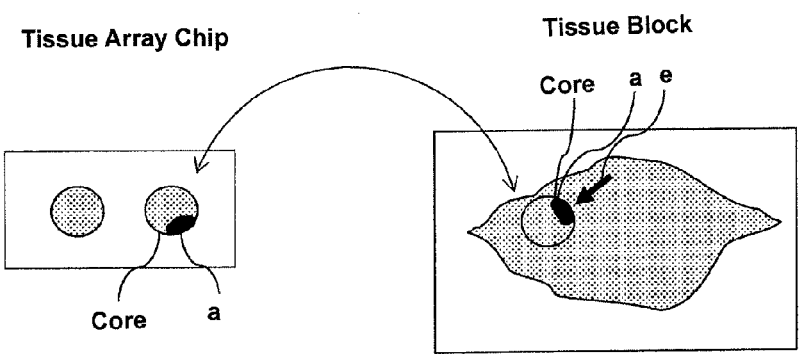
FIG. 14 includes explanatory views illustrating positional relationship between a site of interests included in a core and a site of interests formed on a tissue block surface.

FIG. 10(a) is a diagram showing a tissue array chip according to the present example, and (b) a diagram showing a tissue array chip obtained by the conventional punching step. Though the pieces of tissue had to possess an array configuration in the conventional tissue array chip, there were very many defects of pieces of tissue in portions surrounded by undulating lines in the figure. In addition, while the pieces of tissue had to possess a circular shape, there were many pieces of tissue partially broken as shown by an arrow. On the other hand, according to the tissue array chip of the present example, a tissue array chip that had plural spiral pieces of tissue t4 having an array configuration was obtained. The pieces of tissue t4 emerged in the tissue array chip without being substantially broken and, therefore, a very high effect was obtained as compared with the conventional process of collecting cores by punching.

FIG. 10(c) is an enlarged view of pieces of tissue t4 on the tissue array chip fabricated by the present example, and (d) an enlarged view of the pieces of tissue on the tissue array sheet fabricated by the conventional process of collecting cores by punching. The conventional pieces of tissue had a circular shape and were collected from lopsided regions. On the other hand, the pieces of tissue in the present example had a spiral shape and were collected widely from dispersed regions.

FIG. 10(e) is a partially enlarged view of the spiral piece of tissue t4 emerging in the tissue array chip of the present example. A site of interests was contained in the piece of tissue at the position indicated by an arrow. According to the conventional collection of cores by punching, such a site of interests could not be found unless it should be contained in a single point to be punched. The pieces of tissue t4 of the present example had a spiral shape and were collected from a region more dispersed than ever to enable the probability of finding the site of interests to be heightened. Thus, a very high effect could be obtained.

Incidentally, though the present embodiment has been described using the paraffin-embedded tissue block as an example, the tissue block to be used is not limited thereto. For example, a frozen tissue block having tissue frozen may be used. In this case, an embedding agent called a compound is used instead of paraffin. It is preferred that the tissue is frozen in a state embedded in the compound and that the aforementioned processes are performed in a cooled environment capable of maintaining the frozen state. The tissue to be used is not limited insofar as it is body tissue. In addition, the aforementioned processes and systems may appropriately be modified within the object of the present invention.

What is claimed is:

1. A process of fabricating a tissue array, comprising:
    a step of slicing a tissue block to obtain sheet-form pieces of tissue,
    a step of rolling each of the sheet-form pieces closely around a guide member to form a spiral shape tissue around the guide member, and
    a step of inserting the spiral shape tissues in an axial direction into holes arrayed in a base block.

2. A process of fabricating a tissue array according to claim 1, further comprising a step of cutting the spiral shape tissues to have a predetermined length in the axial direction, before or after the step of inserting the spiral shape tissue into the base block.

3. A process of fabricating a tissue array according to claim 1, further comprising a step of slicing the tissue array in the base block in a direction perpendicular to the axial direction to have a spiral shape in cross section.

4. A process of fabricating a tissue array according to claim 1, wherein the tissue block is retained in paraffin, and the tissue block with the paraffin is sliced in the slicing step.

* * * * *